(12) United States Patent
Sengelaub et al.

(10) Patent No.: US 10,354,136 B2
(45) Date of Patent: Jul. 16, 2019

(54) HEAD MOUNTED EYE TRACKING DEVICE AND METHOD FOR PROVIDING DRIFT FREE EYE TRACKING THROUGH A LENS SYSTEM

(71) Applicant: APPLE INC., Cupertino, CA (US)

(72) Inventors: Tom Sengelaub, Berlin (DE); Walter Nistico, Berlin (DE); Matthias Nieser, Berlin (DE); Martin Haller, Berlin (DE); Denis Williams, Krefeld (DE)

(73) Assignee: APPLE INC., Cupertino, CA (US)

( * ) Notice: Subject to any disclaimer, the term of this patent is extended or adjusted under 35 U.S.C. 154(b) by 0 days.

(21) Appl. No.: 15/555,441

(22) PCT Filed: Nov. 6, 2015

(86) PCT No.: PCT/EP2015/075972
§ 371 (c)(1),
(2) Date: Sep. 1, 2017

(87) PCT Pub. No.: WO2016/138969
PCT Pub. Date: Sep. 9, 2016

(65) Prior Publication Data
US 2018/0032812 A1    Feb. 1, 2018

(30) Foreign Application Priority Data
Mar. 3, 2015  (EP) .................................. 15157451

(51) Int. Cl.
*G06K 9/00* (2006.01)
*G06G 5/00* (2006.01)
(Continued)

(52) U.S. Cl.
CPC .......... *G06K 9/00604* (2013.01); *A61B 3/113* (2013.01); *G06F 3/013* (2013.01);
(Continued)

(58) Field of Classification Search
USPC ....... 382/100, 103, 106–107, 128, 162, 168, 382/173, 181, 209, 219, 232, 254, 274,
(Continued)

(56) References Cited

U.S. PATENT DOCUMENTS 6,637,883 B1   10/2003  Tengshe et al.
8,235,529 B1    8/2012  Raffle et al.
(Continued)

FOREIGN PATENT DOCUMENTS

CN          10432226 A     1/2015

OTHER PUBLICATIONS

International Search Report and Written Opinion for PCT/EP2015/075972 dated Feb. 1, 2016.
(Continued)

*Primary Examiner* — Seyed H Azarian
(74) *Attorney, Agent, or Firm* — Fernando & Partners, LLP; William J. Higley

(57) ABSTRACT

The invention relates to a method and a head mounted eye tracking device (10a, 10b) for determining at least a feature of an eye (12), wherein the eye tracking device (10a, 10b) comprises a capturing device (C) for capturing light reflected by the eye (12) and an optical component (14; E, E1, En, E2) capable of altering a propagation direction of the light passing through the optical component (14; E, E1, En, E2). The eye tracking device (10a, 10b) is configured such that when fixed to the head of the user the light captured by the capturing device (C) has passed through the optical component (14; E, E1, En, E2) and constitutes at least part of an image and the feature is determined on the basis of the image in dependency of an information about a relative position between the eye (12) and the head mounted eye tracking device (10a, 10b).

16 Claims, 2 Drawing Sheets

Figure 1:
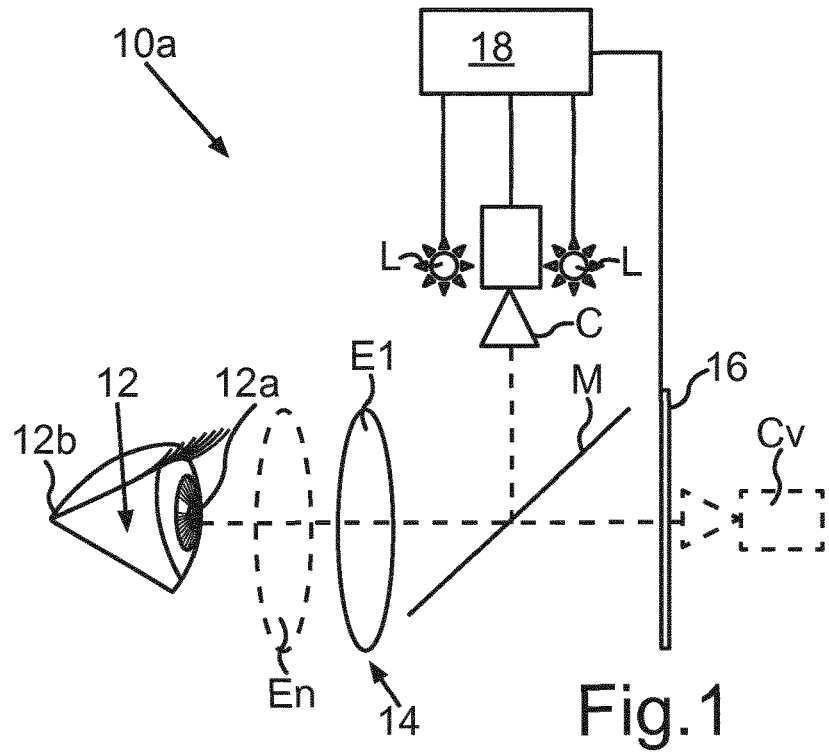

(51) Int. Cl.
  *A61B 3/113* (2006.01)
  *G06F 3/01* (2006.01)
  *G06T 7/73* (2017.01)
  *G06T 7/246* (2017.01)
  *G06T 7/80* (2017.01)
  *A61B 3/00* (2006.01)
  *A61B 3/14* (2006.01)

(52) U.S. Cl.
  CPC ............ *G06K 9/0061* (2013.01); *G06T 7/248* (2017.01); *G06T 7/251* (2017.01); *G06T 7/74* (2017.01); *A61B 3/0025* (2013.01); *A61B 3/14* (2013.01); *G06K 2209/21* (2013.01); *G06T 7/80* (2017.01); *G06T 2207/30201* (2013.01)

(58) Field of Classification Search
  USPC .......... 382/276, 282–291, 305, 321; 345/156
  See application file for complete search history.

(56) References Cited

U.S. PATENT DOCUMENTS

| | | |
|---|---|---|
| 9,727,130 B2 | 8/2017 | Onuki |
| 2003/0123027 A1 | 7/2003 | Amir et al. |
| 2013/0300653 A1* | 11/2013 | Lewis .................... A61B 3/113 345/156 |
| 2014/0003738 A1* | 1/2014 | Williams ............... A61B 3/113 382/282 |
| 2014/0071400 A1 | 3/2014 | Gao |
| 2014/0099623 A1 | 4/2014 | Amit et al. |
| 2014/0361984 A1* | 12/2014 | Kim ........................ G06F 3/013 345/156 |
| 2015/0002394 A1* | 1/2015 | Cho .................... G02B 27/0093 345/156 |
| 2015/0035744 A1 | 2/2015 | Robbins et al. |
| 2015/0130714 A1 | 5/2015 | Onuki |
| 2016/0210503 A1* | 7/2016 | Yin .......................... G06F 3/00 |

OTHER PUBLICATIONS

International Preliminary Report on Patentability for PCT/EP2015/075972 completed on Jun. 13, 2017.

Chinese Patent Application No. 201580078102.8, Office Action dated Aug. 7, 2018.

* cited by examiner

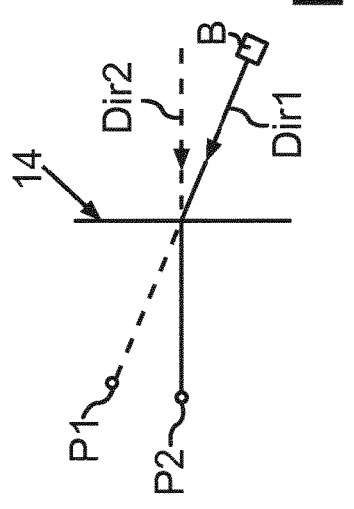
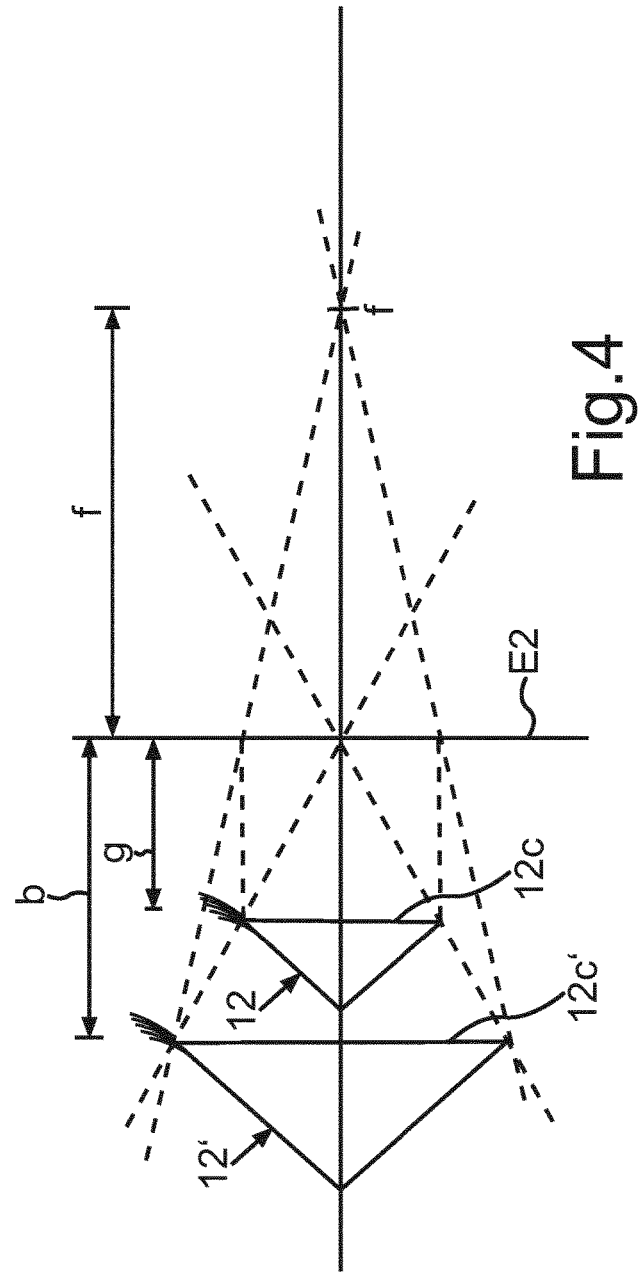

HEAD MOUNTED EYE TRACKING DEVICE AND METHOD FOR PROVIDING DRIFT FREE EYE TRACKING THROUGH A LENS SYSTEM

The invention relates to a head mounted eye tracking device for determining at least one first feature of at least one eye, wherein the head mounted eye tracking device comprises at least one capturing device for capturing light reflected by at least one eye of a user and at least one optical component capable of altering a propagation direction of light passing through the optical component. Furthermore, the invention relates to a method for determining at least one first feature of at least one eye of a user by means of a head mounted eye tracking device.

There are head mounted eye tracking devices known from the prior art, which can comprise a frame that can be mounted to the head of a user and lenses inserted into the frame through which the user can look. Usually eye tracking devices comprise cameras which capture images of the eyes of a user and therefrom determine the gaze direction. These cameras can be placed in the frame and have a direct path to the user's eye. Such configurations have the disadvantage that cameras only have a side view onto the eye, at least for certain gaze directions, and eye features are more difficult to capture. This reduces the tracking accuracy. Furthermore, these cameras can be seen by the user and might be disturbing or occluding parts of the visual field.

Also there are known head mounted displays with integrated eye tracking devices. Head mounted displays usually comprise a display, which is mounted to the head of a user by means of a frame, for example. Images shown on the displays can be projected onto the eyes of a user by means of lenses or lens systems. Also there are head mounted devices known from the prior art, in which the camera is hidden from the user and is observing the user's eye through a lens system. These devices use appearance based, interpolating eye tracking approaches, which have the big drawback that the calibration of these eye tracking devices is invalidated when the relative position of the device with respect to the user's eye is changed, for example if the head mounted eye tracking device slips slightly. This results in a loss of accuracy after movement.

Therefore it is the object of the present invention to provide a head mounted eye tracking device and a method for determining at least one first feature of at least one eye of a user by means of a head mounted eye tracking device, which provides more flexibility in positioning components of the head mounted eye tracking device and at the same time avoids detrimental impact on the tracking accuracy.

This object is solved by a head mounted eye tracking device and a method for determining at least one feature of at least one eye of a user by means of a head mounted eye tracking device with the features of the independent claims. Advantageous embodiments of the invention are presented in the dependent claims.

According to the invention the head mounted eye tracking device is configured such that, when fixed to the head of a user, the light captured by the capturing device has passed through the at least one optical component before and/or after it had been reflected by the at least one eye of the user and constitutes at least part of an image. Thereby, the eye tracking device is configured to determine the at least one first feature on the basis of the image and in dependency of an information about a relative position between the at least one eye and the head mounted eye tracking device.

So advantageously, a change in a relative position between the at least one eye and the head mounted eye tracking device can be taken into account when performing eye tracking, so that no calibration has to be repeated when a change of the relative position takes place and at the same time the eye tracking quality is not negatively influenced. Furthermore, as the captured image is constituted at least at part by light that has passed through the optical component this set up allows for much more flexibility in positioning the components of the head mounted eye tracking device. Thereby, the capturing device, which can comprise one or more cameras or image sensors, and/or light sources of the head mounted eye tracking device, if any, can be positioned behind the optical component with regard to the viewing direction of the user. This additionally allows for hiding these other components from the user in very beneficial way. Moreover, this has the great advantage that these other components can be optimized in their positions so that a higher tracking quality and accuracy can be achieved. Additionally this allows for positioning the optical component closer to the eyes of the user so that also the visual perception of the surrounding of the user or images shown on a display device of the eye tracking device can be improved.

The information about the relative position between the eye and the head mounted eye tracking device moreover allows for a drift free localization of the at least one first feature of the at least one eye, even when components of the head mounted eye tracking device, like light sources or the capturing device, are positioned behind the optical component. Moreover, the relative position between the at least one eye and the head mounted eye tracking device is to be understood as the relative position between the eye as a whole and the eye tracking device. The relative position between the eye tracking device and the head of the user would be an equivalent characterization, so that instead of the eye tracking device being capable to determine the at least one first feature on the basis of the image and in dependency of an information about a relative position between the at least one eye and the head mounted eye tracking device one could also say that the eye tracking device is capable of determining the at least one first feature on the basis of an information about a relative position between the head of the user and the head mounted eye tracking device.

In general, the at least one optical component can comprise and/or can be configured as a lens, a prism, a spherical lens, an aspherical lens, a free-form lens, a waveguide, a lens system, or an optical system comprising one or more of the named lenses and/or prisms. The at least one optical component also can comprise and/or can be configured as any combination of above named elements and/or systems. Especially, the at least one optical component comprises a refractive optical component and/or a reflective optical element. Such imaging optics relate objects and images mathematically, so that for example the information about the relative position between the eye and the tracking device can also be derived from the image itself when knowing the mathematical relation or an approximation thereof or in general at least one information about the optical component. Moreover, the head mounted eye tracking device can comprise one or more further optical components additionally to the at least one optical component. These further optical components can also be configured as or comprise above named lenses, prism, reflective optical elements like mirrors, and so on.

Furthermore, it is preferred that the optical component is positioned in front of the eye. So the user can see through the optical component and the optical component can project the user's surrounding or an image on a display onto his/her eyes. This is especially advantageous if the head mounted eye tracking device at the same time is configured as a head mounted display or in other words also comprises a display for displaying images to the at least one eye.

Therefore it is a preferred embodiment of the invention that the eye tracking device comprises a display device configured to display images, preferably wherein the head mounted eye tracking device is configured such that light originating from the display device at least in part passes through the at least one optical component and impinges on the at least one eye, especially when the head mounted eye tracking device is fixed to the head of the user. So the optical component can advantageously be used to project images shown on the display or displays into almost the complete field of view of the user. Furthermore, the display can be configured as so called bidirectional display, which is configured to display and capture images at the same time. Therefore, the display of the head mounted eye tracking device can comprise and/or be configured as the capturing device of the head mounted eye tracking device, which facilitates an especially compact configuration of the head mounted eye tracking device.

Moreover, the information about the relative position can be derived in several ways. There are advantageous and simple ways to derive this information directly from the captured images. To do so, it is beneficial to know something about the optical component, like its imaging properties and/or above named mathematical relation and/or approximation thereof. This information can be defined and be known to the head mounted eye tracking device, e.g. stored in a storage device of the eye tracking device or a storage device the eye tracking device can be coupled with and/or implemented in an algorithm performed by a processing unit of the eye tracking device for eye tracking, or the head mounted eye tracking device can be configured to derive this information, for example, by performing a calibration procedure. The information about the relative position can also be determined otherwise, for example without knowing anything about the optical component. The head mounted eye tracking can be configured such that images of the eye and/or face of the user can be captured that comprised features that do not change in their position relative to the eye tracking device when the user changes his/her gaze direction, except the relative position between the user and the eye tracking device changes. For example, eye corners of the eye can be detected. If the eye tracking device determines the position of the pupil based on the captured images, this position changes in the images if the user changes his/her gaze direction, but the position of the eye corners does not change due to changes in the gaze direction. So it can be determined whether the change of a position of the pupil is due to a movement of the eye tracking device relative to the user's eye, because in this case the position of the eye corner would have changed as well, or the change in the position of the pupil is due to the user changing his/her direction of view, because in this situation, the position of the eye corner does not change. Instead of eye corners, also other features of the eye or face can be detected, like eyebrows, the nose or the like. The head mounted eye tracking device can also comprise a component for detecting the information about a relative position, like a change in the relative position, for example, a sensor, especially a proximity sensor, an accelerometer, or an inertial measurement unit.

Consequently, there are many simple and favorable ways to determine the information about the relative position between the eye and the eye tracking device and to use this information for correcting or rescaling determined eye features.

Besides, the head mounted eye tracking device can be configured to perform model based eye tracking and/or appearance based eye tracking. In both cases it is advantageously possible to determine the at least one feature of the at least one eye also if the capturing device and/or light sources are positioned behind the optical component without having a negative influence on the eye tracking quality.

Furthermore, the head mounted eye tracking device can be configured to determine the at least one first feature as at least one of the group of a pupil, a sclera, a limbus, an iris, a cornea, a cornea center, an eyeball center, a pupil center, a pupil diameter, a pupil characteristic, a limbus characteristic, a sclera characteristic, an iris characteristic, a characteristic of a blood vessel, a cornea characteristic, an eyeball characteristic, a gaze direction, a point of gaze, an orientation, a position and an eyelid closure of the at least one eye. Also more of these features can be determined, for example, to determine the gaze direction first the eyeball center and the pupil center can be determined and therefrom a gaze vector can be calculated. Also other combinations of the features of above named group or single features of above named group can be used to calculate the gaze direction vector.

In this context the point of gaze is the point a user is looking at. It can be calculated by intersecting the gaze direction vectors of each eye of the user. If a two dimensional surface the user is looking at is known, e.g. the person is looking at a screen or display that may be integrated into the head mounted eye tracking device, the point of gaze can be calculated as the intersection of the gaze direction of the left eye or of the right eye or of an averaged gaze direction of the left and the right eye with this surface. Also more advanced methods for calculating the binocular point of gaze may be used, e.g. taking into account the users physiognomy or conditions such as nystagmus or strabismus in a statistical, stochastic or higher level model.

In an advantageous embodiment of the invention the eye tracking device is configured to perform a localization of a second feature of the at least one eye in dependency of the information about the relative position between the eye and the eye tracking device based on the image and to determine the at least one first feature on the basis of the localization of the at least one second feature. As already mentioned, to determine the gaze direction as first feature, second features like a pupil, cornea or eyeball, can be determined to do so. In general the second features can also be at least one in the above named group.

A localization of a second feature in this context can be understood as the localization of the second feature in real space or as the localization of the second feature in the image. For example, if the eye tracking device performs appearance based or interpolating eye tracking, usually in a calibration procedure the eye tracking device captures several images of the eyes of the user while he/she is looking at predefined calibration points and the eye tracking device establishes a mapping that maps for example the pupil position in the image to a corresponding point of gaze on a display.

Thereby no localization of the pupil in real space has to be performed. Now it is very advantageous to take into account the information about the relative position between the eye and the eye tracking device, because then the eye tracking device is capable of differentiating the two situations whether the position of the pupil in the image has changed due to a change in gaze direction or due to a movement of the eye tracking device relative to the user's head. To discern these both situations eye features like eye corners can be detected additionally as already mentioned.

Furthermore, the localization of the second feature can also be performed as a localization of the second feature in real space by determining two or three real space coordinates of the second feature with respect to the eye tracking device.

Thereby it is very beneficial when the eye tracking device is configured to perform the localization as a 3D localization. Thereby the position of the eye, the position of a cornea or a position of the pupil or other eye features can be determined very accurately, so that also the gaze direction can be calculated precisely.

This 3D localization is preferably performed in conjunction with model based eye tracking. Therefore, it is another very advantageous embodiment of the invention when the head mounted eye tracking device is configured to determine the at least one first feature of the at least one eye based on a model of the at least one first and/or at least one second and/or at least one third feature of the at least one eye. For example the eye orientation can be inferred from the perspective deformation of the pupil contour or limbus contour and a distance to the respective eye can be calculated from the dimensions in the image of eye features which do not change dynamically, such as limbus major and minor axis, or eyeball radius. So for example, if the eyeball radius is assumed to be the same for every user and is known, by determining the eyeball radius from an image and by setting this determined radius in relation to the actual known radius the distance of the eye from the camera or the capturing device in general can be determined. For the case that the camera is seeing the eye through the at least one optical component the optical properties of the optical component have to be taken into consideration. If the focal length, a scaling factor or any other imaging property of the optical component is known, forms and dimensions detected in the captured image can be mapped to the corresponding real forms and dimensions. Therefrom e.g. the 3D-position and/or 3D-orientation of the eye or other eye features can be derived and by this a 3D-localization of these features is performed.

Consequently, it is very advantageous that according to another embodiment of the invention the head mounted eye tracking device is configured to determine the at least one first feature and/or to perform the localization of the at least one second feature and/or to provide the information about the relative position based on an information about an optical property of the at least one optical component. This optical property can be a focal length, e.g. of a single lens of the optical component, an effective focal length, e.g. of a total optical system of the optical component, a scaling factor, imaging properties, refraction properties, diameters of lenses of the optical component or surface properties. These properties don't have to be known exactly but can also be approximated by certain approximations of the optical properties of the optical component and/or its single optical elements. For example surface properties of lenses and/or free form lenses and or prisms of the optical component can be described by a polynomial description and/or mesh representation and so on. The refraction properties of lenses can be described by Snell's law and that of thin lenses of the optical component can be e.g. approximated by the thin lens approximation. If the optical component comprises more than one optical element then also different approximations or mathematical descriptions for each optical element can be used.

These optical properties of the optical component can be pre-given, e.g. this information is already included in the algorithm used for eye tracking, or this information can be derived by the eye tracking device itself, for example, by a calibration procedure. Beneficially, this information about the optical property of the optical component can also be used or included in feature search criteria for searching eye features in the image. For example for detecting the pupil in the image the eye tracking device searches for circle-like objects or elliptical objects having certain dimensions in the image. If now these dimensions in the image are changed due to the optical component, this can be considered when searching for pupil candidates so that the eye tracking device searches for circle-like objects or elliptical objects which have dimensions that are rescaled on the basis of the optical property of the at least one optical component. Also forms of objects in the image can change due to the optical properties of the optical component, so this can be considered similarly.

As a result, the at least one first feature and also the localization of the at least one second feature can be performed very accurately using information about the optical property of the optical component. Information about the optical property can also be used to provide the information about the relative position between the eye and the eye tracking device, especially because this information can be derived directly from the captured images. If the eye tracking device is configured to localize eye features in real space using the knowledge about the optical property of the optical component, the eye tracking device consequently is capable of determining the relative position between the eye and the eye tracking device and moreover also to determine changes of that relative position. So changes between the head mounted eye tracking device and the user's head do not have any negative influence on the eye tracking performance, in the contrary, by having more flexibility in positioning components of the eye tracking device and especially performing model based eye tracking the eye tracking quality, e.g. gaze accuracy, can even be enhanced in comparison to known eye tracking systems.

Furthermore, the head mounted eye tracking device can be configured to map a position of the at least one second feature in the image and to modify the mapping in dependency of the information about the relative position between the eye and the eye tracking device. Especially, the eye tracking device can map the position of the second feature in the image to the position of the second feature in real space, e.g. determining the position of the pupil in real space based on the position of the pupil detected in the image. Also features like the gaze direction and/or point of gaze can be calculated on the basis of the image and be mapped to the corresponding direction and/or position in real space. This can be done for example by considering the optical property of the optical component when mapping. On the other hand the position of the at least one second feature in the image can also be mapped directly to the corresponding value of the first feature. For example, the eye tracking device can determine the position of the pupil in the image and map this position to a corresponding gaze direction. For defining this map e.g. a calibration or simulation procedure can be performed. To achieve that changes in the relative position between the eye tracking device and the eye do not invalidate this map, it is very advantageous to modify the mapping in dependency of the information about the relative position between the eye and the eye tracking device. This way, the map stays always valid and correctly maps the second feature, even if changes in the relative position between the eye and the eye tracking device take place. These changes can for example be detected by determining eye corners in the image, additional sensors, like a gyroscope, a proximity sensor, an accelerometer, or an inertial measurement unit, or any combination of these sensors and/or by deriving this information on the basis of the captured images.

The head mounted eye tracking device can also be configured to determine an actual gaze direction from a first gaze direction as the at least one second feature of the at least one eye, wherein the information about the optical property of the at least one optical component is used to correct the first gaze direction derived from the image to provide the actual gaze direction as the first feature of the eye. Advantageously this is a very simple and easy way to determine the gaze direction of the user. For example, the eye tracking device is configured to determine the gaze direction based on the captured images in a conventional way ignoring the influence of the optical component. Then this determined first gaze direction can be mapped to the actual gaze direction by a map that considers the optical property of the at least one optical component. For example this map can be derived by a calibration procedure or be predefined, e.g. as a look-up table. As this map considers the optical property of the optical component, changes of the relative position between the eye tracking device and the eye are considered automatically. This also works with other eye features different from the gaze direction. So also other features of the eye, like the cornea, pupil position, and so on, can be determined on the basis of the image and be mapped to the actual features using the map considering the optical property of the optical component.

So it is very advantageous when the head mounted eye tracking device is configured to determine the at least one first feature of the at least one eye and/or to perform the localization of the at least one second feature by deriving a property of the at least one second feature of the at least one eye from the image captured by the capturing device wherein the information about the optical property of the at least one optical component is used to map the property of the at least one second feature derived from the image to provide the at least one first feature and/or the localization of the at least one second feature. This property can be a dimension, position and/or form of the second feature, like a cornea diameter or a form of the pupil contour.

Furthermore, the head mounted eye tracking device can be configured to derive the information about the optical property of the at least one optical component from calibration results of a calibration procedure for calibrating the head mounted eye tracking device. If the optical component comprises a very complex optical system with lenses or prisms and/or free form lenses, that cannot be described in a mathematical way so easily or the calculation time for calculating the gaze direction on the basis of complex mathematical formulas describing the optical component would take too long, it is very beneficial to derive the optical property from a calibration procedure. This way the optical property of the optical component is implicitly derived from the calibration procedure and for example on the basis of the calibration results a map can be defined which maps the detected or determined features to the actual ones. Also a model for the optical component can be used, like a lens model with parameters for a thickness and/or radius of curvature, wherein these parameters of the model can be fitted during the calibration procedure so that the model describes the optical property of the actual optical component approximately or accurately.

Therefore, it is a preferred embodiment of the invention that the head mounted eye tracking device is configured to derive the information about the optical property of the at least one optical component from a model of the at least one optical component, especially wherein the model of the at least one optical component models the altering of light passing through the at least one optical component. As mentioned, this model can be used to fit model parameters during a calibration procedure. But furthermore, this model can also be pre-given, for example as an approximation of the optical properties and imaging properties of the real optical component. If, for example, the optical component comprises a lens having a thickness much smaller than its radius of curvature, then the thin-lens approximation might be used to model the altering of light passing through the optical component. Also other approaches might be used for that model to simplify complex lens systems and for describing the optical properties of the optical component.

According to a further embodiment of the invention the head mounted eye tracking device is configured such that, when fixed to the head of a user, a light path from the at least one eye of the user to the capturing device is altered by the at least one optical component. So images of the eye features the capturing device captures are influenced by the optical component. The influence of the optical component on the eye features in the image can be compensated, e.g. by the methods previously described. Having the light path from the eye to the capturing device altered by the at least one optical component or in other words having the optical component in the light path from the eye to the capturing device has very great advantages with respect to the flexibility of positioning the capturing device. First of all, especially if the head mounted eye tracking device comprises a display device, it is very advantageous to have the optical component as close as possible to the eye of the user as then the projection of the images shown on the displays onto the eyes can be optimized. Also lenses with smaller diameter can be used for projecting these images to the whole field of view of the user if these lenses are closer to the eye of the user. In such a setup it is very hard to position a camera or a capturing device in between the eye and the optical component. Consequently it is very beneficial to be able to position the capturing device somewhere behind the optical component and eye tracking can be performed on the one hand with higher tracking quality and on the other hand with the possibility of placing the optical component as close as possible to the eye. Furthermore, by positioning the capturing device behind the optical component makes it possible to hide the capturing device from the user so that the user is not disturbed by seeing the capturing device.

Furthermore, the head mounted eye tracking device can comprise at least one light source for illuminating at least part of the at least one eye when the head mounted eye tracking device is fixed to a head of a user. Preferably this light source is configured to cause at least one reflection on the at least one eye. Those reflections, like glints or other Purkinje images, can be used for eye tracking, especially, to more accurately determine the positions and orientations of eye features. These one or more light sources can for example emit infrared light, which has the advantage that it cannot be seen by the user so that it does not disturb him/her.

In this case the capturing device is preferably configured to be sensitive for at least the infrared spectral range. The capturing device captures the reflection produced by the at least one light source and localizes features of the eye using the position of these reflections with regard to the eye or eye features, e.g. by modeling the cornea as a spherical mirror, which enhances the tracking quality as i.e. explained in the book Remote Eye Tracking by Hammond, Chapter 7.

In general, the head mounted eye tracking device can be configured such that the light path extends from the at least one light source to the at least one eye and from the at least one eye to the at least one capturing device, wherein the at least one optical component is positioned in that light path, especially so that a light propagating along the light path passes through the at least one optical component. So either the capturing device or the at least one light source or even both can be placed behind the optical component with regard to a viewing direction of the user so that the flexibility of optimized positioning of the components of the eye tracking device is enhanced even more.

For the same reason it is preferred that the head mounted eye tracking device is configured such that when fixed to the head of a user light propagating from the at least one light source to the at least one eye of the user on the light path is altered in its propagation direction by the at least one optical component. In this embodiment the light source is placed behind the optical component from the perspective of the user so that light emitted by the light source first passes through the optical component and then hits the eye and produces reflections. If also the capturing device is placed behind the optical component the light reflected by the eye passes through the optical component again before it is captured by the capturing device, so that at least part of the light that is captured by the capturing device and constitutes the image has passed twice through the optical component. Also configurations are possible in which a capturing device directly captures images of the eye without the optical component being positioned in between but only the one or more light sources are positioned behind the optical component so that light emitted by the light sources passes through the optical component, is reflected by the eye afterwards and then is detected directly by the capturing device. In this case only the part of the captured image which relates to the caused reflections on the eye is influenced by the optical component, wherein other eye features are not influenced. In this case the information about the optical property of the optical component is used for determining the at least one first feature of the eye only with respect to the reflections. For example, if point-like and/or circle-like reflections are produced, the optical component can change the size and form and position of these reflections, which advantageously can be considered when determining the gaze direction or other features. The light sources can also be configured to produce structured reflections or light patterns, e.g. in an annular shape, on the eye which are then similarly influenced in their size, form or position by the optical component, which can again considered when determining eye features.

According to a further embodiment of the invention the head mounted eye tracking device comprises a planar optical element, preferably a mirror, especially a beam splitting mirror with regard to different spectral ranges and/or a dichroic mirror and/or a hot mirror, wherein the head mounted eye tracking device is configured such that, when fixed to the head of a user, at least part of the light propagating from the at least one eye of the user to the capturing device is reflected by the planar optical element, and preferably passes through the at least one optical component before being reflected by the planar optical element. This planar optical element has the great advantage, that even more flexibility with regard to the positioning of the capturing device is provided. The planar optical element is capable of redirecting the light path from the eye to the capturing device, so that it is possible to position the capturing device such, that it cannot be seen by the user. In this context, it is very advantageous to have the planar optical element as a dichroic mirror, for example as a hot mirror, which can be transmissive for a predefined spectral range and reflective for second spectral range, e.g. the infrared spectral range different from the first spectral range. This way, when the mirror is transmissive for the visible wave length range the user can look through the mirror without seeing the mirror. At the same time the capturing device can capture infrared images of the eye that are constituted by light that is reflected by the mirror and which then advantageously can be used for determining the at least one first feature of the eye. Alternatively or additionally, this planar optical element can also be used to redirect light from the one or more light sources of the eye tracking device for producing the reflections on the eye of the user. In a similar way also these light sources can be hidden from the user and can be optimized in their positioning.

If the head mounted eye tracking device is configured also as head mounted display the planar optical element can be positioned such and configured such that the light originating from the display passes through the mirror, through the optical component and then impinges on the eye so that though the planar optical element is positioned in the view path of the user to the display, he/she can view the image on the display uninterruptedly. Furthermore, the mirror can be positioned on the optical axis of the optical component and preferably a surface normal of the mirror is inclined by an angle, especially 45° degrees, towards the optical axis. This way the optical path is redirected by a right angle by means of the planar optical element.

Furthermore, the head mounted eye tracking device can be configured such that, when fixed to the head of a user, light propagating on the light path from the at least one light source to the at least one eye of the user is reflected by the planar optical element, and preferably passes through the at least one optical component after being reflected by the mirror. So also the light sources can be hidden from the user and nevertheless can be placed in an optimal position for illuminating the eye.

The invention also relates to a method for determining at least one feature of at least one eye of a user by means of a head mounted eye tracking device with at least one capturing device for capturing light reflected by the at least one eye and at least one optical component, wherein a propagation direction of light passing through the at least one optical component is altered. Therein, when the head mounted eye tracking device is fixed to the head of a user, light is captured by the at least one capturing device, wherein the light has passed through the optical component before and/or after it had been reflected by the at least one eye of the user and constitutes at least part of an image, wherein the at least one first feature is determined on the basis of the image and in dependency of an information about a relative position between the at least one eye and the head mounted eye tracking device.

The preferred embodiments and advantages described with regard to the head mounted eye tracking device according to the invention correspondingly apply to the method according to the invention. Especially, the head mounted eye tracking device according to the invention can be used for performing the method for determining the at least one feature with the at least one eye according to the invention. Furthermore, described embodiments of the head mounted eye tracking device according to the invention constitute further steps of the method according to the invention.

Even though the invention is described by referring to the at least one eye of the user, the invention similarly applies to both eyes as well. E.g. the eye tracking device can comprise two capturing units, each for one eye, or a common capturing unit for both eyes, two optical components, each for one eye, or a common optical component.

Moreover the determination of the at least one first or other features can be performed for each eye as described above.

The preferred embodiments refer to the optical component which can be fixed in position or dynamic within the head mounted eye tracking device. If the optical component comprises several optical elements, each of these optical elements can either be fixed or changeable in it's position. The position can be known or unknown according to the explanations above. Further the at least one optical component or at least one optical element of the optical component can have a static or dynamic characteristic, e.g. in case of a lens the refractive power can change over time and space (e.g. in case of a liquid lens), this state can be known or unknown to the head mounted eye tracking device.

In the following, advantageous embodiments of the present invention are described in more detail with reference to the accompanying drawings.

Figure 2:
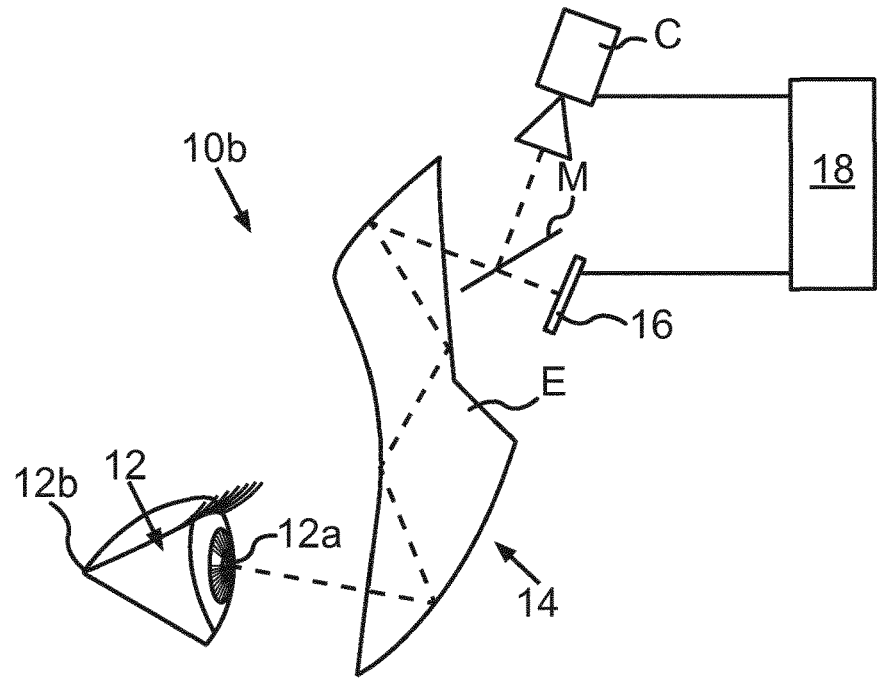

They show in:

FIG. 1 a schematic illustration of a head mounted eye tracking device according to a first embodiment of the invention;

FIG. 2 a schematic illustration of a head mounted eye tracking device according to a second embodiment of the invention;

FIG. 3 a schematic illustration of the principle of ray-tracing used for describing the optical properties of the optical component of the head mounted eye tracking device according to an embodiment of the invention; and FIG. 4 a schematic illustration for reconstructing the eye in a virtual coordinate system for use in an eye tracking device according to an embodiment of the invention.

FIG. 1 shows a schematic illustration of a head mounted eye tracking device 10a according to a first embodiment of the invention. Generally, the head mounted eye tracking device 10a comprises a capturing device C, which can comprise one or more cameras or sensors for taking pictures of the eye 12 of a user wearing the head mounted eye tracking device 10a. Furthermore, eye tracking device 10a comprises an optical component 14 which can comprise one or more lenses, prisms or other optical elements. In this example, the optical component 14 comprises a lens E1 and optionally further lenses En, which is illustrated by the dashed lens contour in FIG. 1. Also optionally the eye tracking device 10a can comprise one or more light sources L, of which two are shown in FIG. 1 exemplarily. As further optional components the eye tracking device 10a can comprise a hot mirror M and a display device 16. Moreover, the eye tracking device 10a comprises a processing unit 18 for processing the captured images and determining at least one feature of the eye 12.

The optical component 14 is placed between the capturing device C and the user's eye 12 with regard to the optical path from the eye 12 to the capturing device C so that at least some eye features in the image captured by the capturing device C are altered by the optical component 14, e.g. in their form, size and/or position. For example, the lens E1 between the capturing device 10 and the eye can magnify the pupil 12a in the captured image.

The light sources L can produce reflections on the cornea, especially in a structured way, like in an annular form, and/or a point-like way and/or circle-like way. The light path from the light sources L to the eye 12 is in this setup also altered by the optical component 14. Especially in this configuration the light emitted by the light sources L is also reflected by the mirror M, passes through the optical component 14 and impinges on the eye 12. The images captured by the capturing device C are processed by the processing unit 18 and features of the eye 12 are detected.

The hot mirror M facilitates more flexibility with regard to the capturing device C and the light sources L and still makes a central view of the capturing device C onto to the eye possible. This is illustrated by the virtual camera Cv. The view of the capturing device C corresponds to the view of a camera at the position of the virtual camera Cv without the mirror M.

In other embodiments of the invention, for example for a different use of the head mounted eye tracking device 10a, e.g. for medical or diagnosis purpose, the capturing device C could also be placed in the position of the shown virtual camera Cv and the mirror M and the display device 16 can be omitted. The capturing device C can also comprise more than one camera or sensors in different places. The capturing unit C could also be placed to have direct view onto the eye 12 without having the optical component 14 in between and only the light sources L are placed such that the light path from the light sources L to the eye 12 passes through the optical component 14. On the other hand, also the light sources L could be placed such, that they illuminate the light directly without having the optical component 14 in between and the capturing device C is positioned as shown.

The light sources L and/or the capturing device C can even be placed between elements of the optical component 14. So there are many possibilities for optimal positioning of the components of the eye tracking device 10a by which the optical properties and the eye tracking quality can be optimized.

FIG. 2 shows a schematic illustration of a head mounted eye tracking device 10b according to another embodiment of the invention. In this embodiment an optical component 14 comprises a free-form lens E and light captured by the capturing device C propagates from the eye 12 through the free-form lens E, is reflected by the hot mirror M and then captured by the capturing device C. In general any kind of optical waveguide can be used additionally to or instead of this free-form lens E. During the light is propagating through the optical component 14 it is several times internally reflected by the surface of the free-form lens E, for which purpose the lens E optionally can comprise a reflective coating on parts of its surface. Furthermore, here again the eye tracking device 10b can comprise a display unit 16, wherein light from the display unit 16 passes through the hot mirror M, through the free-form lens E and finally impinges on the eye 12. Here also the eye tracking device 10b can optionally comprise one or more light sources, which are not shown in this case. These optional light sources can be positioned so that they illuminate the eye 12 directly and/or through the free-form lens E. Using a free-form lens E has the advantage that the eye tracking device 10b can be built even more compact and at the same time components of the eye tracking device like the capturing device C can be hidden from the user.

In these situations when the capturing device C captures light that has passed through the optical component 14 to constitute at least part of the image of the eye 12, different from state of the art eye tracking techniques, the processing unit 18 now has to deal with the fact that the observed eye 12, or the observed glints, in the image is not a direct projection of the real eye 12 onto the sensors of the capturing device C, but maybe altered by the optical component 14. In order to compensate for this, several different techniques can be applied, which are explained in more detail in the following with regard to a setup, in which the capturing device C is placed behind the optical component 14 but which applies for light sources L being placed behind the optical component 14 as well.

First of all, the optical properties of the optical component 14 can be taken into account implicitly by performing a calibration procedure and based on this calibration a map can be defined which maps the positions of certain eye features in the captured images, like the position of the pupil, to the corresponding real eye features, like the position of the pupil 12a in real space, or to other eye features like the gaze direction. The general problem with this approach is that once the user moves his/her head relative to the eye tracking device 10a, 10b, for example if the head mounted eye tracking device 10a, 10b slightly slips, then eye tracking would not work accurately anymore. The invention advantageously solves this problem by taking into account at least one information about relative position between the eye tracking device 10a, 10b and the eye 12 when determining features of the eye 12. This can be done for example by detecting eye corners 12b or other features that do not move with regard to the eye tracking device 10b if the user changes his/her gaze direction except the eye tracking device 10a, 10b changes its position with respect to the user's head. This movement would lead to images in which the captured eye corners 12b also comprise a different position from that of images taken before. For example the position shift of the eye corners 12b can be determined in the images and used for shifting back the detected position of the pupil 12a in the image.

Also other methods like raytracing, reconstructing the eyes in virtual coordinate systems, undistorting the camera image, using a virtual camera and/or reconstructing the gaze on a virtual stimulus plane can be used and are explained in the following.

Most of these methods use a model of the optical component 14, but this is not a necessity. There are several models for the optical component 14 or parts thereof, like models for a lens or lens systems or other optical elements as part of the optical component 14, and this invention does not rely on a specific one. Any model which describes the refracting properties of the optical component 14 or its elements or approximates them can be used. For example, the optical component 14 can be modeled as a set or a combination of single elements, wherein each element can be described by a paraxial lens model using the paraxial approximation, especially for thin lenses, a spherical lens model, a thick lens model and/or a free-form model. A free-form model comprises a closed surface, which can be represented in terms of elementary shapes like ellipsoid, plane, box, paraboloid, and so on, which are combined using Constructive Solid Geometry laws, like intersection, subtraction, union, clipping of multiple shapes and so on, as well as in terms of through tessellation, linearization, approximation with a mesh of triangles or polygons or second order surfaces. But it may also be possible to describe the whole optical system of the optical component 14 or a subset of the optical component 14 with a simplified model or, if this is not available, to rely on pre-computed or otherwise existing representations of the light path through the optical component 14, like a raytracing for one or more specific camera poses with respect to the optical component 14.

FIG. 3 shows a schematic illustration of the principle of raytracing for use in a head mounted eye tracking device 10a, 10b according to an embodiment of the invention, especially for taking into account the optical properties of the optical component 14. An idea of this method is to trace the rays back from the capturing unit C, e.g. a camera, or of a light source, which is denoted with a reference sign B in FIG. 3, into the direction Dir1 of the detected features, that are represented by the observed point P1 in FIG. 3, until they hit the optical component 14. Then, the ray at the optical component 14 is refracted and one obtains a new outgoing ray, especially a refracted ray, which can be described by a point P2 on that ray and its new direction Dir2. How to do the refraction depends on the model of the optical component 14, e.g. on a lens model. The raytracing can also be beneficial in the other direction when one would be interested in the refracted image of a known point on e.g. the camera sensor. For example for thin lenses of the optical component 14 the thin lens approximation can be used for modeling the light refraction. Furthermore, for the capturing unit C a pinhole camera model can be used, meaning the Capturing unit comprises camera with a camera sensor and an aperture that is assumed to have an infinitesimal opening, so that for each point and/or pixel of the camera sensor one light direction can be assigned, from which light has passed through the aperture and had impinged on that point and/pixel. In an embodiment the thin-lens approximation is used for the optical component 14 to do a bidirectional correction of rays in order to correct light rays derived from e.g. the pinhole camera model as well as to project 3D points to the camera sensor in a way as it would be perceived by the camera when observing that point through the at least one optical component 14.

In some embodiments, the position and orientation in space of the capturing device C, e.g. the camera, of each lens element E1, En, E of the optical component 14, of each light source L and eventually of other optical elements such as mirrors M are known. In other embodiments the position of some or all of such elements might not be known and in that case a calibration procedure can be performed in order to find the unknown values of said parameters which minimize the overall calibration error. Hereby, the calibration is not necessarily explicit, i.e. not necessarily performed by building a model of the components, but can also be implicit by using a global mapping, like a homography or even being determined and/or derived and/or decomposed from a user calibration.

The coordinates of points and/or directions in the real word (meaning metric points) are determined with the help of known or calibrated and/or mapped coordinates and properties of the optical setup by means of a applying a series of raytracing transformations. These transformations can be performed by applying the law of reflection at reflective surfaces, that is the angle of incidence with respect to the surface normal and the angle of reflection are the same, and/or by applying Snell's law at refractive surfaces. That refracted ray can be used in an algorithm which reconstructs the eye 12 or features of the eye 12 instead of using the original ray coming from the capturing device C, e.g. a camera or image sensor.

In the case that the eye tracking device 10*a*, 10*b* comprises one or multiple light sources L, the assumed direct light path causing for example a reflection on the cornea is corrected by the described raytracing. This covers all possible setups of cameras, light sources L, mirrors and the eye 12 with respect to the optical component 14, e.g. a lens system. For example, capturing device C, e.g. the camera, can be on one side, the eye 12 and the light sources L on the other side. But the camera and the light sources L could also be on the same side or even somewhere in the middle of the lens system of the optical component 14.

In general three types of raytracing can be performed. The first is backward raytracing, which is done by originating from the coordinates of the points, for example, a glint or cornea reflection, on a camera image plane, e.g. using the pinhole camera model. Such a ray is then cast until it hits the surface of components of the optical component 14 and goes through a chain of refractions and reflections. Second is forward raytracing for the rays originating directly from the light sources L or features of the eye 12, and after a chain of refractions and reflections hitting the camera's image sensor. A third is mixed forward and backward raytracing, wherein rays coming from the light sources L and rays which correspond to seen features in the image are considered and used to find the parameters of the eye model.

In theory, this approach can be used for almost all eye tracking algorithms which so far do not consider having optical components 14 in the path to the user by replacing rays coming from the camera by rays which are altered by the optical component 14. As an example, we show an approach of using raytracing to reconstruct the real eye position and gaze direction. The idea of doing backwards raytracing is more general and not only limited to this algorithm.

As an example, it is possible to consider a set of possible eye states/hypotheses (e.g. particle filters) where each state hypothesis contains the full set of coordinates of the eye components which are included in the model, for example eye position and orientation, including visual axis to optical axis shift and so on. It can be then for each said hypothesis been performed a raytracing for each feature which is expected to be seen in the image. Such feature can be the pupil center and/or contour, iris center and/or contour, eye corners, eye lids, cornea reflections etc. So the expected location of said features in the (virtual) image can be found. The likelihood of said hypothesis can then be computed as a function of the distance of each of its features (in 2D) from the detected features in the real image, applying a statistical measurement error model.

FIG. 4 shows a schematic illustration of reconstructing the eye in virtual coordinate system for use in a head mounted eye tracking device 10*a*, 10*b* according to an embodiment of the invention, especially for taking into account the optical properties of the optical component 14. In this example the optical component 14 is exemplarily configured as a thin lens E2. When looking with the camera through this lens E2 onto a user's eye, the camera will see a virtual image of such when positioned within the focal length of the lens E2 of the head mounted eye tracking device 10*a*, 10*b* or head mounted display. This is illustrated in FIG. 4. Here, 12*c* denotes the limbus of the real eye 12 and E2 the thin lens in thin lens approximation. Furthermore, f denotes the focal length of the lens E2, wherein the focal length f is larger than the object distance g so that an image of the real limbus 12*c* is produced as a virtual image 12*c*' at the image distance b.

Any eye tracking method which is based on capturing images of the eye can be applied to that image ignoring that the observed eye is distorted by the lens, or in general an optical system, of the optical component 14. The output of such algorithm will be eye parameters, like position and/or orientation of the eye, gaze and so on, which are not reflecting the true state of the eye, but describe a virtual eye. The goal of this method is to calculate corresponding real eye parameters from observed virtual parameters. A principle is to take any point of the reconstructed eye, for example the eye center, cornea position, pupil and/or limbus center, contour point of the limbus, and so on, in the virtual coordinates and transform them to real coordinates. The transformation is fully defined by the optical component 14, e.g. by the lens or lens system thereof, and can be for example implemented as a look-up table, (non-) linear mapping, or interpolations. Either the transformation can be explicitly computed like for a simple thin lens model, or it can be obtained numerically, for example, by performing an off-line raytracing simulation of the whole optical system of the optical component 14.

One possibility is to define a range of possible eyeball locations and eye orientations. This set can be sampled by a grid of finite locations and/or orientations, with arbitrary spacing and distribution. Raytracing is then performed for each sample and the coordinates of each relevant eye feature are stored in a look-up table against the ground truth coordinates of the simulation. For example, when having this look-up table one could look up 2D cornea reflections determined on the image sensor, which sees a virtual image of the eye, and get the corresponding 3D coordinates of the cornea center, in real metric coordinates.

Another method is to undistort the camera image. The virtual image of a user's eye which is seen through the optical component 14, e.g. through a lens or lens system, is mathematically related to the real image one would see if there would be no optical component 14, e.g. lens or lens system, in between, at least for a known or assumed distance of the eye form the optical component 14 which can be determined using other sensors like proximity sensors. The goal is to undistort this image, that is to calculated corresponding real 2D-points from observed virtual 2D-points. The principle is to determine a directly observable eye feature, like the limbus, or part of a directly visible eye feature, like the contour point of the limbus, in the virtual eye image and to correct the point (or direction) afterwards using the properties of the one or more lenses of the optical component 14 or other optical elements of the optical component 14.

Another method would be to use a virtual camera. Instead of correcting the observed virtual image by the real, for example pinhole, camera, one could construct a virtual camera which models the optical component 14, e.g. lenses, of the head mounted eye tracking device 10*a*, 10*b* as part of the camera.

Another possibility is to use such simulation to create an approximate virtual camera representing the complex optical setup, described by a predefined set of parameters, which may include virtual 6D coordinates of the virtual camera, field of view horizontal and vertical, principal axis shift, tilt of the image plane with respect to the optical axis of the virtual camera. In addition, it can be computed a 2D distortion model of the virtual camera, which can have polar components, polynomial, or other non-linear model. Alternatively the raytracing can be done just to pre-compute a table or to learn the parameters of a model or function, which maps the relative 2D coordinates between the eye feature (for example 2D pupil center to 2D cornea reflections center) to 3D eye position and/or orientation of the eye.

A further method is to reconstruct the gaze on a virtual stimulus plane. Instead of correcting for the optical component 14, e.g. the lens, one ignores the optical component 14 and eye tracking is done via traditional algorithm (not including a lens). This means the gaze is calculated based on the altered image and the final output of the eye features (for example the gaze) is corrected afterwards.

This method can be an simple work-around to achieve valid gaze data without dealing too much with the lens. Furthermore, the approach is not limited in the number of optical elements of the optical component 14. First, eye tracking with the optical component 14 in front of the camera is performed and the eye position and gaze orientation, as well as all other relevant features are reconstructed ignoring the existence of the optical component 14. If necessary for later steps the calculated 'virtual' parameters can be mapped, using a possibly predetermined relation, into 'real' coordinates.

The transformation can be done either directly with vector algebra taking the properties of the lens into account. Another way can be to compute the mapping of real to virtual coordinates, to performing a tessellation of the virtual stimulus plane by direct raytracing and then to apply an interpolation. This method can be applied also when the optical component 14 comprises more than one lens or even a complex optical system.

All in all the invention makes it possible to gain flexibility in positioning the capturing device and illumination sources within the head mounted eye tracking device and to hide the components from the user. Furthermore a capturing device of the eye tracking device can be positioned so that feature visibility of eye features is optimized over different eye positions and motions.

The invention claimed is:

1. A method comprising:
at an electronic device including a processor, non-transitory memory, and a camera:
capturing, with the camera, a first image of an eye of a user at a first time;
determining, using the processor based on the first image, a position of a gaze-variant feature of the eye of the user at the first time and a position of a gaze-invariant feature of the eye of the user at the first time, wherein the position of the gaze-variant feature changes if the user changes a gaze direction of the eye and the position of the gaze-invariant feature does not change if the user changes the gaze direction of the eye;
determining, using the processor, a first gaze direction of the eye based on the position of the gaze-variant feature at the first time;
capturing, with the camera, a second image of the eye of the user at a second time;
determining, using the processor based on the second image, an initial change in the position of the gaze-variant feature from the first time to the second time;
determining, using the processor, a change in the position of the gaze-invariant feature from the first time to the second time;
determining, using the processor, a corrected change in the position of the gaze-variant feature based on the initial change in the position of the gaze-variant feature and the change in the position of the gaze-invariant feature; and
determining, using the processor, a second gaze direction of the eye based on the corrected change in the position of the gaze-variant feature.

2. The method of claim 1, wherein determining the change in the position of the gaze-invariant feature includes determining a change in the position of the gaze-invariant feature in the second image as compared to the first image.

3. The method of claim 1, wherein determining the change in the position of the gaze-invariant feature includes receiving data from a motion sensor.

4. The method of claim 1, wherein determining the second gaze direction based on the corrected change in the position of the gaze-variant feature includes modeling the refractive properties of at least one refractive optical element.

5. The method of claim 1, wherein the gaze-variant feature includes at least one of a pupil center or an iris center.

6. The method of claim 1, wherein the gaze-invariant feature includes at least one of an eye corner, and eyebrow, or a nose.

7. The method of claim 1, further comprising:
capturing, with the camera, a third image of a second eye of the user at the first time;
determining, using the processor, a third gaze direction of the second eye based on the third image;
capturing, with the camera, a fourth image of a second eye of the user at the second time; and
determining, using the processor, a fourth gaze direction of the second eye based on the fourth image and the change in the position of the gaze-invariant feature.

8. The method of claim 7, further comprising determining a point of gaze based on the second gaze direction of the eye and the fourth gaze direction of the second eye.

9. An apparatus comprising:
a camera to capture a first image of an eye of a user at a first time and capture a second image of the eye of the user at a second time; and
a processor to:
determine, based on the first image, a position of a gaze-variant feature of the eye of the user at the first time and a position of a gaze-invariant feature of the eye of the user at the first time, wherein the position of the gaze-variant feature changes if the user changes a gaze direction of the eye and the position of the gaze-invariant feature does not change if the user changes the gaze direction of the eye;
determine a first gaze direction of the eye based on the position of the gaze-variant feature at the first time;
determine, based on the second image, an initial change in the position of the gaze-variant feature from the first time to the second time;
determine a change in the position of the gaze-invariant feature from the first time to the second time;
determine, a corrected change in the position of the gaze-variant feature based on the initial change in the position of the gaze-variant feature and the change in the position of the gaze-invariant feature; and
determine a second gaze direction of the eye based on the corrected change in the position of the gaze-variant feature.

10. The apparatus of claim 9, wherein the processor is to determine the second gaze direction based on the corrected position by modeling the refractive properties of at least one refractive optical element.

11. The apparatus of claim 9, wherein the gaze-variant feature includes at least one of a pupil center or an iris center.

12. The apparatus of claim 9, wherein the gaze-invariant feature includes at least one of an eye corner, and eyebrow, or a nose.

13. The apparatus of claim 9, wherein the camera is further to capture a third image of a second eye of the user at the first time and capture a fourth image of a second eye of the user at the second time, wherein the processor is to determine a third gaze direction of the second eye based on the third image and determine a fourth gaze direction of the second eye based on the fourth image and the change in the position of the gaze-invariant feature.

14. A non-transitory computer-readable medium encoding instructions which, when executed by a processor, cause a processor to perform operations comprising:
   determining, based on a first image of an eye of a user taken at a first time, a position of a gaze-variant feature of the eye of the user at the first time and a position of a gaze-invariant feature of the eye of the user at the first time, wherein the position of the gaze-variant feature changes if the user changes a gaze direction of the eye and the position of the gaze-invariant feature does not change if the user changes the gaze direction of the eye;
   determining a first gaze direction of the eye based on the position of gaze-variant feature at the first time;
   determining, based on a second image of the eye of the user taken at a second time, an initial change in the position of the gaze-variant feature from the first time to the second time;
   determining a change in the position of the gaze-invariant feature from the first time to the second time;
   determining a corrected change in the position of the gaze-variant feature based on the initial change in the position of the gaze-variant feature and the change in the position of the gaze-invariant feature; and
   determining a second gaze direction of the eye based on the corrected change in the position of the gaze-variant feature.

15. The non-transitory computer-readable medium of claim 14, wherein determining the change in the position of the gaze-invariant feature includes determining a change in position of the gaze-invariant feature in the second image as compared to the first image.

16. The non-transitory computer-readable medium of claim 14, wherein determining the second gaze direction based on the corrected change in the position of the gaze-variant feature includes modeling the refractive properties of at least one refractive optical element.

* * * * *